(12) United States Patent
Casset

(10) Patent No.: US 8,233,981 B2
(45) Date of Patent: Jul. 31, 2012

(54) CALCULATION OF THE ATRIOVENTRICULAR DELAY FOR AN ACTIVE IMPLANTABLE METAL DEVICE

(75) Inventor: Cyrille Casset, Saint-Selve (FR)

(73) Assignee: Sorin CRM S.A.S., Clamart (FR)

( * ) Notice: Subject to any disclaimer, the term of this patent is extended or adjusted under 35 U.S.C. 154(b) by 377 days.

(21) Appl. No.: 12/621,314

(22) Filed: Nov. 18, 2009

(65) Prior Publication Data

US 2010/0125308 A1 May 20, 2010

(30) Foreign Application Priority Data

Nov. 19, 2008 (FR) ..................... 08 06462

(51) Int. Cl.
*A61N 1/36* (2006.01)
(52) U.S. Cl. ............................................. 607/9
(58) Field of Classification Search .............. 607/4, 9, 607/19, 18, 27, 28; 600/508, 509
See application file for complete search history.

(56) References Cited

U.S. PATENT DOCUMENTS

| | | |
|---|---|---|
| 5,318,594 A | 6/1994 | Limousin et al. |
| 7,164,946 B2 | 1/2007 | Amblard et al. |
| 2006/0293715 A1 | 12/2006 | Plicchi et al. |
| 2007/0179541 A1 | 8/2007 | Prakash et al. |
| 2011/0093027 A1* | 4/2011 | Renesto et al. ............ 607/9 |

FOREIGN PATENT DOCUMENTS

| | | |
|---|---|---|
| EP | 0 515 319 | 9/2003 |
| WO | WO 2005/089866 | 9/2005 |

OTHER PUBLICATIONS

FR, Foreign Search Report (Annexe Au Rapport De Recherche Preliminaire; Ralatif A La Demande De Brevet Francais No. FR 0806462 FA 715105), Jul. 24, 2009.

* cited by examiner

*Primary Examiner* — Brian T Gedeon
(74) *Attorney, Agent, or Firm* — Orrick Herrington & Sutcliffe, LLP

(57) ABSTRACT

An active implantable medical device including circuits for calculating an atrio ventricular delay (AVD) period. The device is able to detect the atrial and ventricular events; calculate an AVD and to start the AVD on detection of a spontaneous or paced atrial event. The device is able to deliver a low energy ventricular stimulation pulse at the expiration of the AVD in the absence of a detected spontaneous ventricular event. To calculate the AVD, the device uses an acceleration sensor to deliver an endocardiac acceleration (EA) signal representative of the movements produced by the contractions of the atrial cavity; and analyzes the EA signal to identify and isolate in the EA signal a component corresponding to the fourth peak of endocardiac acceleration (PEA4) associated to the atrial activity, and to calculate the AVD based on a parameter of this component.

16 Claims, 3 Drawing Sheets

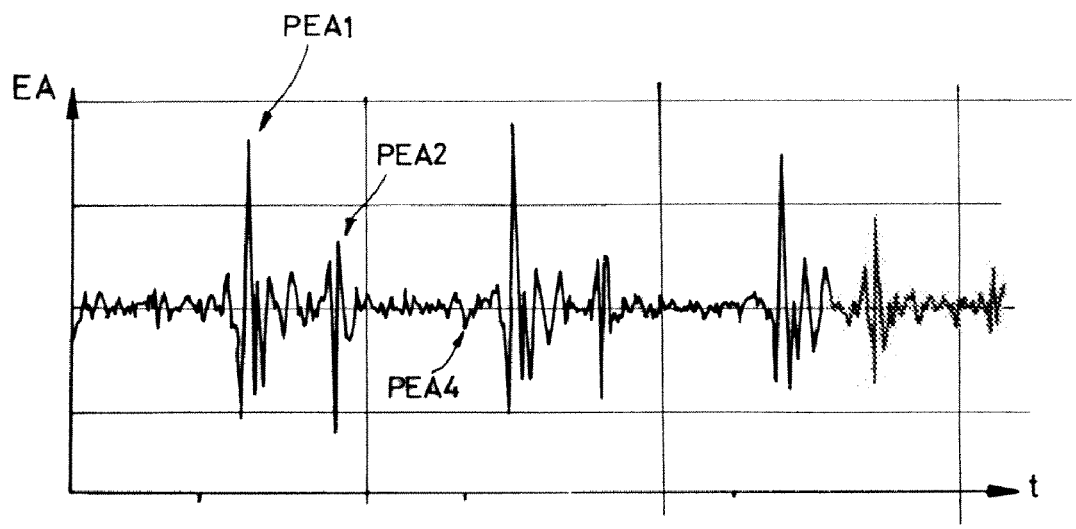
FIG_1
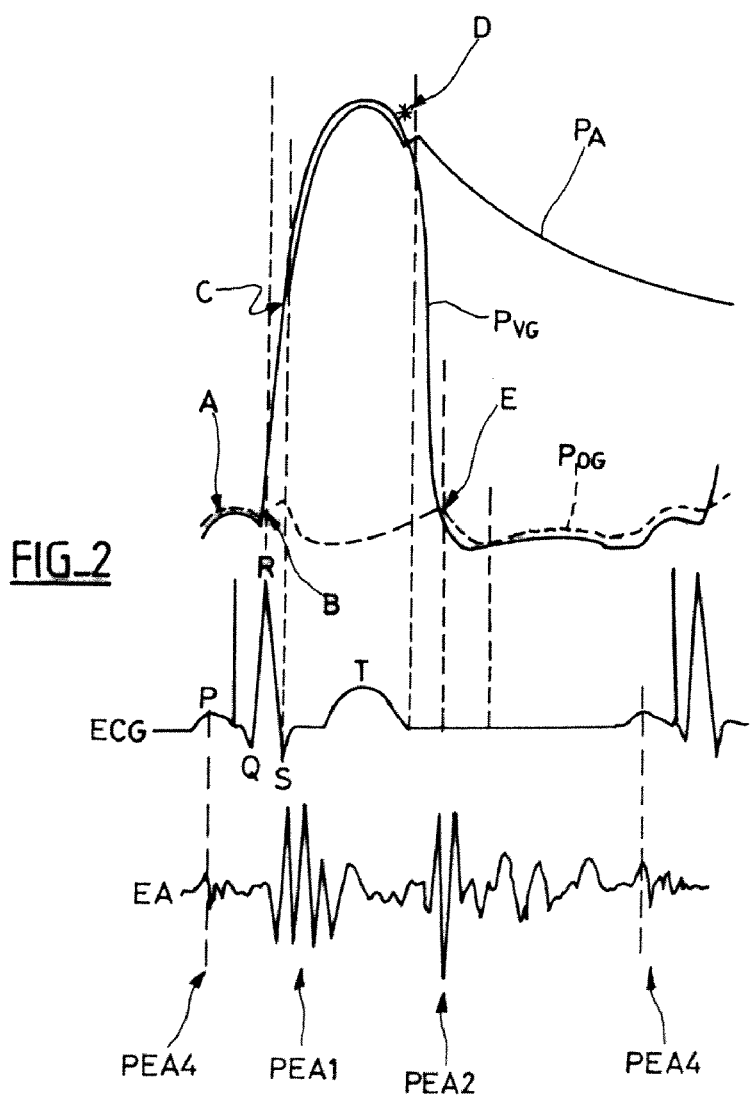
FIG_2

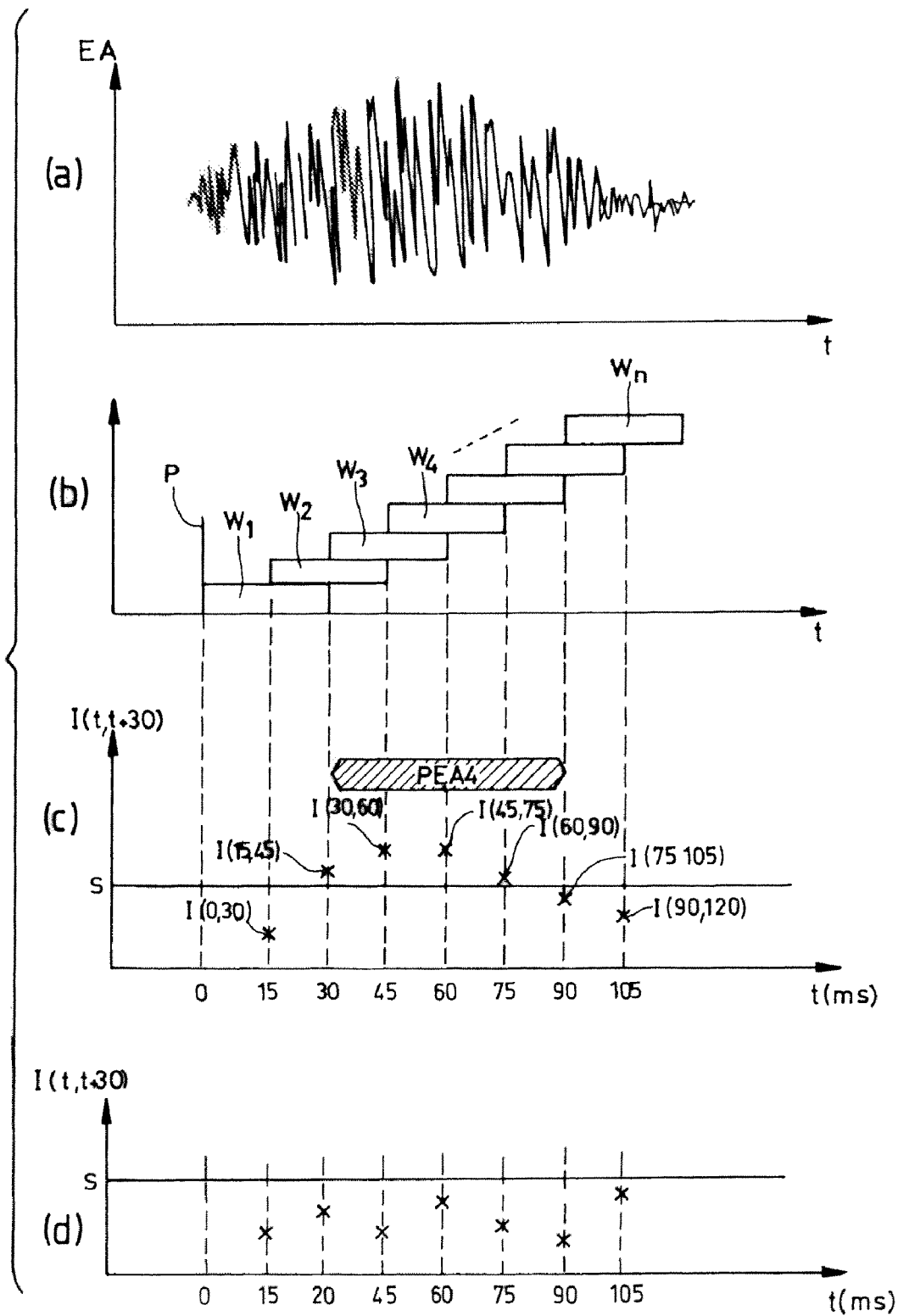

FIG_4
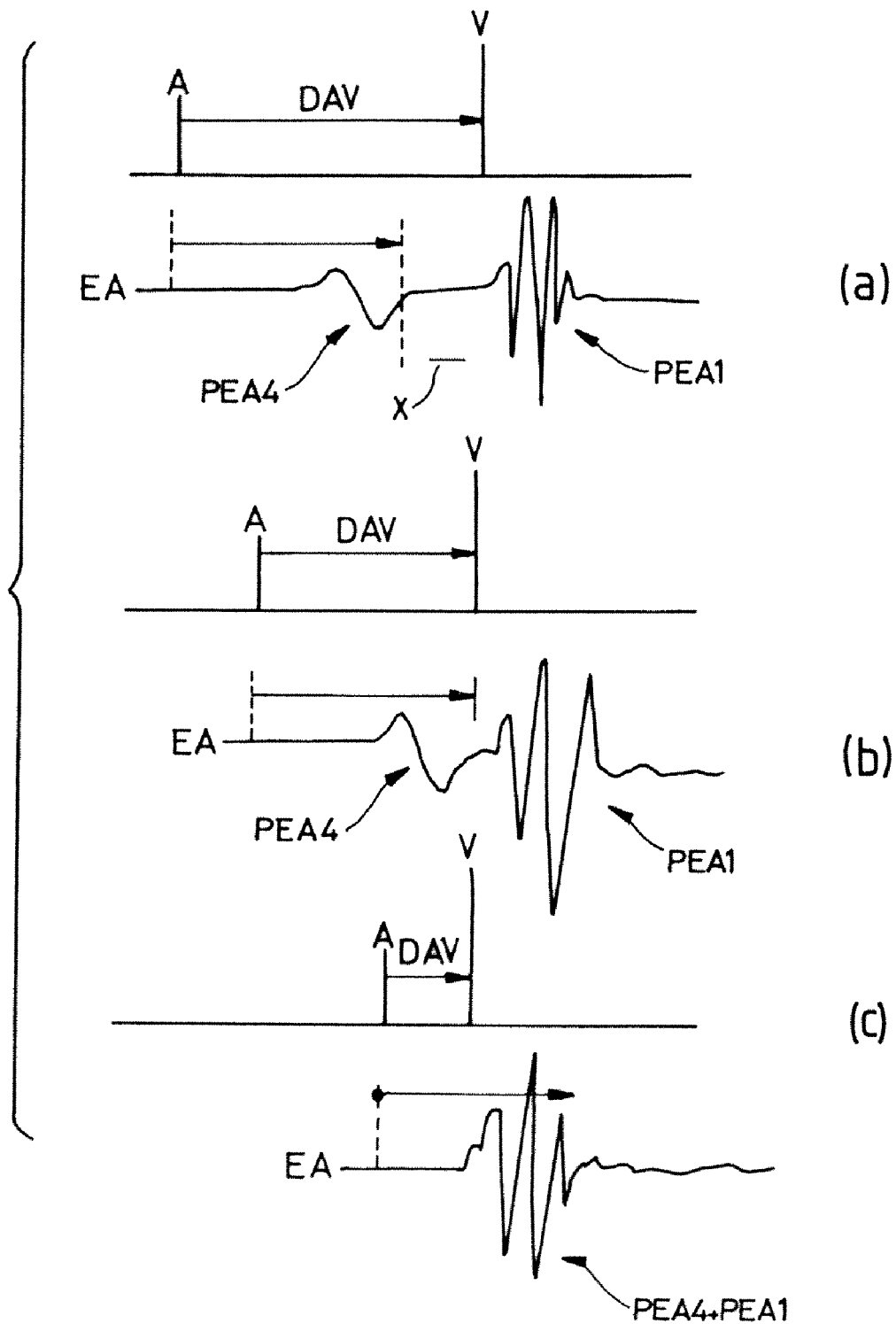

CALCULATION OF THE ATRIOVENTRICULAR DELAY FOR AN ACTIVE IMPLANTABLE METAL DEVICE

CROSS REFERENCE TO RELATED APPLICATIONS

This application claims the priority of French Patent Application No. 08/06462, filed on Nov. 19, 2008. The entire disclosures and contents of the above application are hereby incorporated by reference.

FIELD OF THE INVENTION

The present invention relates to "active implantable medical devices" as defined by the Jun. 20, 1990 Directive 90/385/EEC of the Council of the European Communities, and particularly to implantable devices that continuously monitor heart rhythm and, in the case of a rhythm disorder detected by the device, if necessary, deliver to the heart electrical pulses for cardiac stimulation, resynchronization, cardioversion and/or defibrillation. The invention even more particularly relates to those implantable devices that have at least one detection/stimulation lead for the atrium or both atria, mainly of the following types: atrial single chamber, atrioventricular dual chamber or "multisite" triple or quadruple chamber pacemaker or defibrillator.

BACKGROUND OF THE INVENTION

In a dual chamber operating mode, following an atrial event, whether the atrial event is a spontaneous (detected P wave) or a stimulated (application of an A pulse) depolarization, the implantable device monitors the ventricular activity and at the same time, starts counting a period called the "atrio-ventricular delay", generally designated "AVD" or "DAV." If, after the AVD period no spontaneous ventricular activity (detected R wave) has been detected, then the device triggers a stimulation of the ventricle (application of a V pulse).

It should be understood that, although the invention will be described in the context of an implantable pacemaker device that includes channels for stimulation of and sensing in the atrium and the ventricle, and that can operate at least in the conventional AAI and DDD pacing modes, it is not so limited and is more broadly applicable to implantable devices. Initially, the operating mode of the pacemaker is the AAI mode with monitoring of the ventricular activity. The control algorithm then looks for the presence or absence of ventricular activity, which in this case could allow a suspected atrioventricular block (AVB), with the potential to switch to the DDD mode, namely dual chamber stimulation with atrio-ventricular association, that is to say calculating and applying an AVD for the ventricular controlled stimulation. This mode is also called the "AAIsafeR" mode.

EP 0 488 904 A1 and its counterpart U.S. Pat. No. 5,318,594, and EP 1 346 750 A1 and its counterpart U.S. Pat. No. 7,164,507 (both assigned to ELA Medical), describe such implantable devices with AAI/DDD automatic mode switching. In any case, it is important to accurately define the AVD duration.

Indeed, from a cardiac mechanics viewpoint, the AVD must be sufficiently long to allow the atrium to contract completely and thereby empty the blood it contains into the ventricle, and the ventricular contraction ideally must therefore occur after the atrial contraction is fully finished. But the ventricular contraction should not occur too long after the atrium is emptied, because if too long the AVD might dissociate the atrio-ventricular system, with a risk of triggering retrograde conduction arrhythmias, or reducing the effectiveness of the haemodynamics of the cardiac cycle. As the atrial contraction ends the ventricular filling, the time between the end of this filling and the beginning of the ventricular emptying is a "dead" or "lost" time from an haemodynamics point of view.

It is therefore important to improve the adaptation of the AVD for each patient, so that the start of the ventricular emptying (caused by the stimulation of the ventricle) occurs immediately after the end of the filling of the ventricle by the atrium.

In most of the known implantable pacemaker type devices, the AVD is automatically adjusted according to the detected sinus frequency, with the AVD being able to take various values between a maximum value (corresponding to a base AVD) and a minimum value. The value of the AVD calculated from the sinus frequency is further increased by an additional period if the atrial event is a stimulated event, so as to compensate for the delay between the stimulation and the detection in the atrium.

The basic parameters of the automatic calculation of the AVD are programmed by the practitioner at the time of implantation or during follow-up visits of the patient. In some devices, the AVD may be automatically adjusted by the device after an analysis of the patient's heart rhythm over a long period of time.

However, the programming of these parameters does not take into account the haemodynamics reality of each patient, and, furthermore, do not allow a fine adjustment of the AVD. This is because the calculation of the AVD does not consider whether the atrial contraction was or was not entirely terminated before ventricular pacing had been triggered.

To address this difficulty, the WO 2005/089866 A1 proposes to detect the atrial contraction by an endocardiac acceleration signal delivered by an appropriate accelerometer sensor. Such a sensor may be present on the atrial lead or on another lead, said lead being placed with the sensor directly in the atrium or in another position suitable to detect the signal of endocardiac acceleration (EA) (known as the "EA signal") representative of the contractions of the atrium.

In this alternate approach, the device, after atrial pacing, uses a functional signal—the EA signal—representative of the cardiac mechanics, instead of a signal originated by the electrical propagation of the depolarization wave. This mechanical EA signal can also be exploited as a complement to the electrical signal, as described in US2007/0179541 A1 which proposes to measure and analyze the delay between the electrical and mechanical detections of the atrial contraction.

The WO 2005/089866 A1 suggests, however, to use the EA signal for different purposes, such as an optimization of the AV period in the case of a dual chamber pacing, an optimization of the VV delay in the case of a biventricular pacing for a cardiac resynchronization therapy (CRT), a detection of the capture in a cardiac cavity, etc.

However, as compared to the electrical signal, the component of the EA signal corresponding to the mechanical activity of the atrium not only presents an amplitude much lower than the amplitude of the EA signal corresponding to the mechanical activity of the ventricle, but it also happens much earlier in time. This renders detection of the atrial component and its analysis much more difficult. This situation also is believed to be the reason why, until now, it has not been proposed to use any technique based on the analysis of the atrial component of the EA signal to obtain really exploitable results, despite the interest of obtaining a signal accurately corresponding to the mechanical activity of the heart.

OBJECTS AND SUMMARY OF THE INVENTION

It is, therefore, an object of the present invention to overcome the aforemention difficulty by proposing a calculation of the AVD to directly monitor the progress of the cardiac cycle from a mechanical point of view, to be sure that the contraction of the atrium is actually completed when the ventricular stimulation pulse is delivered to the heart.

The invention is broadly based on the approach that advantageously, mechanically detects the contraction of the atrium, including the timing when this contraction ends, through an endocardial acceleration signal (EA signal) issued by an appropriate accelerometer sensor. Such a sensor may be present on the atrial lead, or on another lead, and either directly placed in the atrium or in another position that allows the sensor to detect the endocardiac acceleration signal representative of the contractions of the atrium.

Indeed, various clinical studies have been conducted which show that the endocardiac acceleration is a parameter which provides comprehensive information on the mechanical heart activity, in the case of normal operation and in the case of a deficient functioning. The endocardiac acceleration, which is measured by an accelerometer coupled to the heart muscle, indeed reflects very precisely and in real time phenomena related to movements of the heart chamber detected (the atrial cavity in the case of the present invention).

Thus, EP 0 515 319 A1 (Sorin Biomedica Cardio SpA) teaches one embodiment of how to detect an EA signal using an endocardial lead incorporating a micro-accelerometer to measure the endocardiac acceleration. It should be noted that, although the present invention describes the analysis of an EA signal as one delivered by an implanted sensor (typically, a sensor placed on an endocardial lead), the invention is more broadly applicable to include an analysis made from an external EA signal detected by a non-invasive sensor. Such an EA signal may be, for example, a signal from an acceleration sensor fixed on the patient's chest at the sternum.

Here and subsequently it should be understood that the term "EA signal" refers to and includes an external EA signal, detected by a suitable non-invasive sensor, an endocardial EA signal detected by an acceleration sensor mounted on a cavity introduced into a patient's heart, or an EA signal issued by an epicardium lead located in direct contact with the myocardium.

Essentially, the invention proposes, after detecting an electrical depolarization signal corresponding to an atrial event (spontaneous or stimulated), to use a functional signal representative of the cardiac mechanics (the EA signal), to calculate an AVD such that the contraction of the atrium is actually completed, and just completed, at the end of the AVD. This is done instead of calculating the AVD on the basis of more or less empirical pre-programmed parameters, or directly recalculated parameters from the analysis of the rhythm and of the atrial and ventricular sequencing.

One aspect of the invention is directed to a device, for example, according to WO 2005/089866 A1, including: means for detecting atrial events; means for detecting ventricular events, means for calculating an atrio-ventricular delay (AVD) and starting said AVD on the detection of a spontaneous or stimulated atrial event, and means for ventricular pacing, able to deliver at the end of the AVD a low energy stimulation pulse in the absence of a detected spontaneous ventricular event.

In accordance with the present invention, the means for calculating the AV delay includes: an acceleration sensor having as an output an EA signal representative of the movements produced by the contractions of the atrial cavity; and means for analyzing EA signal, and identifying and isolating in the EA signal the so-called "EA4" component, corresponding to the fourth peak of endocardiac acceleration associated with the atrial activity, and for calculating the value of the AVD based upon the EA4 component.

In a preferred embodiment, the means for analyzing the EA signal delivered by the sensor further comprises means for determining a parameter of the EA4 component, in particular a parameter that is a function of the moment when the EA4 component ends. The AVD value is then calculated based on this determined parameter of the EA4 component.

Preferably, the AVD can be calculated so that the end of the AVD is concurrent or subsequent to the moment when the EA4 component ends (the so-called "end time"), the end of the AVD being more particularly defined by the end time of the EA4 component.

In an advantageous improvement, the means for analyzing the EA signal also are also able to recognize and isolate in the EA signal the so-called "EA1" component, corresponding to the first endocardial acceleration peak associated with the ventricular activity and to determine a start time of this EA1 component. The value of AVD is then calculated also as a function of the start time of the EA1 component. In a preferred embodiment, the AVD can be calculated based on the time interval between the end time of the EA4 component and the start time of the immediately following EA1 component, and more preferably no that the moment the EA4 component end matches with the start time of the immediately following EA1, or so that the end time of the EA4 component precedes the start time of the immediately following EA1 component by a predetermined time period.

In a preferred embodiment, the means for analyzing the EA signal includes means for quantifying a parameter of the EA signal within at least one analysis time window having a fixed length, this window being triggered after the detection of the atrial event and ending before a ventricular detection or stimulation. Preferably, the quantified parameter can be the energy of the EA signal, integrated over the duration of the analysis time window, and this parameter is quantified for each of a plurality of successive analysis time windows, including successive analysis time windows that are respectively overlapping in time.

In one embodiment, a comparison is made of the quantified EA signal parameter within a given time window to a given threshold S. This threshold S may be a fixed threshold, a configurable threshold, an adaptive threshold recalculated at regular intervals, or an adaptive threshold recalculated on each cycle comprising a valid atrial event. The threshold S can thus be used to distinguish the end time of the atrial contraction.

The acceleration sensor may be an endocardial sensor, an epicardial sensor or an external sensor.

BRIEF DESCRIPTION OF THE DRAWINGS

Further features, advantages and characteristics of the present invention will appear to a person of ordinary skill in the art in view of the following detailed description of a preferred embodiment of the present invention, made with reference to the drawings annexed, in which the same numerical references designate items that are identical or functionally similar from one figure to the next, and in which:

FIG. 1 illustrates an example of endocardiac acceleration EA signals detected during three successive cardiac cycles;

FIG. 2 is a series of three timing diagrams illustrating various signals characterizing cardiac activity during a given cycle;

FIG. 3 is a series of four timing diagrams showing how the representative PEA4 component detection is made according to a preferred embodiment of the invention; and FIG. 4 is a series of three timing diagrams showing an example of the EA signal obtained, respectively, in the case of an AVD which is too long, with a properly adjusted AVD, and with a too short AVD.

DETAILED DESCRIPTION OF THE INVENTION

A preferred embodiment of a device in accordance with the present invention will now be described with reference to the drawings.

As regards its software aspects, the invention can be implemented by suitable programming of the software of a known pacemaker, for example, a cardiac pacemaker or defibrillator/cardioverter, including means for detecting a signal provided by endocardial leads and/or one or more implanted sensors. The invention may be advantageously applied to known implantable devices such as the Reply family of products produced and marketed by ELA Medical (also known as Sorin CRM), Montrouge, France.

These are devices with programmable microprocessor controlled circuits and control logic that are operated to receive, form and process electrical signals received by implanted electrodes, and to deliver stimulation pulses having suitable energy levels to these electrodes. It is possible to transmit to these devices by telemetry software instructions that will be stored and executed in suitable memory to implement the functions and algorithms of the present invention as described herein. The adaptation of these devices to implement the functions of the present invention is believed to be within the abilities of a person of ordinary skill in the art, and therefore will not be described in detail.

As illustrated in FIG. 1, which is an example of endocardiac acceleration (EA) signals collected during three successive cardiac cycles, the EA signal presents during a cardiac cycle two main peaks corresponding to the two major noises (these are known as sounds S1 and S2 of phonocardiogram) that it is possible to recognize in each cycle of a healthy heart:

The first endocardiac acceleration peak ("PEA1"), whose variations are closely related to changes in pressure in the ventricle (the peak amplitude PEA1 is more precisely correlated to the dP/dt maximum positive change in pressure in the left ventricle);

The second endocardiac acceleration peak ("PEA2"), which corresponds to the phase of ventricular isovolumetric relaxation and is produced by the sudden deceleration of the blood mass in movement in the aorta.

The EA signal components EA1 and EA2 are those that correspond to the two endocardiac acceleration peaks, respectively PEA1 and PEA2. The EA signal, however, also contains two additional components, of much lower amplitude, called EA3 and EA4, corresponding to S3 and S4 sounds of the phonocardiogram.

The present invention focuses on the detection and use of the EA4 component, which is directly related to the presence of an atrial contraction. Essentially, the inventor has discovered that the atrial component signal EA4 can be used to manage the settings of a pacemaker linked to the atrial activity and in particular the AVD.

This atrial component presents in particular a peak (herein "PEA4") which, shown in FIG. 1, is located immediately before the PEA1 peak. For this reason, the PEA4 is sometimes "PEA0" by cardiologists, because, from an electrical point of view, the atrial contraction precedes the ventricular contraction. However, if we consider the blood flow that is pumped by the heart muscle, the contraction of the atrium (corresponding to the component EA4) completes the filling of the ventricle in the end of the diastole corresponding to the (EA component) and is therefore, in terms of cardiac haemodynamlos, after the latter—hence the designation "PEA4".

FIG. 2 illustrates the various signals characterizing the activity of the heart during a cardiac cycle, with: the profile of intracardiac pressures a track of a surface electrocardiogram (ECG), and the variations in the endocardiac acceleration signal (EA).

On the profile of intracardiac pressures, the $P_A$ characteristic shows the variations in aortic pressure, the $P_{VG}$ Shows the pressure variations of the left ventricle, the shows the pressure variations in the left atrium. Points A to E correspond to different phases: A, contraction of the left atrium; B, closure of the mitral valve, C, opening of the aortic valve, D, closure of the aortic valve, and E, opening of the mitral valve.

The ECG signal includes successively: the P wave corresponding to the depolarization of the atrium, the QRS complex corresponding to ventricular depolarization, and the T wave corresponding to the ventricular repolarization.

The endocardiac acceleration signal EA, meanwhile, can be broken down as follows: EA4 is the component corresponding to the contraction of the atrium (P wave), followed by the EA1 component, which begins after the QRS complex and is caused by a combination of the closure of atrio-ventricular valves, the opening of the semi-lunar valves and the contraction of the left ventricle. The EA2 component that follows accompanies the end of ventricular systole and is generated by the closure of semi-lunar valves. The EA3 component is not shown.

Referring to FIG. 3, a series of timing diagrams presents an advantageous embodiment of one implementation in accordance with the present invention for the detection of the EA4 component, notably enabling (i) to detect the presence or absence of a PEA4, peak and (ii) if a PEA4 peak is detected to determine the moments of the start and end of this peak.

The chronogram of FIG. 3a shows the EA signal in the period immediately after atrial pacing, said atrial pacing event being indicated by the P marker on the chronogram in FIG. 3b. This event P triggers a first time window W1 (FIG. 3b having a start time of T and a finish time of T+D), for example, with a preselected duration, e.g., D=30 ms. Over the duration of this window WI an index I (T, T+D) or more generally "I" is calculated, e.g., I (0, 30) representative of the EA signal in the interval T=0 to T+D=30 ms. This index I is, for example, determined from the digitized signal values sampled by calculating the integral of the absolute value of this EA signal over this interval W1. The value of the index I for each window thus represents the average power of the EA signal over the duration of that window. In the preferred embodiment, each window is centered on the timing midpoint of the window, here t=15 ms, and is represented by a point on the chronogram represented in FIG. 3c at the abscissa t=15 ms.

This same determination of Index I is repeated for a new window W2, shifted in time relative to window W1 by a predetermined time lag. The time lag may be, for example, 15 ms corresponding to the window duration D divided by two, although other time lags may be used as discussed below. This second determination, therefore, conducted over the interval T=15 to T+D=45 ms for a window W2, gives a new index I (15,45). The determination is thus repeated again for a series of sliding windows W3, W4 . . . Wn, each window being shifted by the same predetermined time lag, e.g., 15 ms in this example, compared to the previous window and generating a series of corresponding indices I3, I4 . . . In. The repetition is continued until one of a ventricular event is detected, the index In crosses downwardly of (i.e., falls below) a threshold S, or a fixed period, typically one hundred milliseconds, expires.

Based on the evaluation described above, it is considered that there is an atrial contraction in the cardiac cycle in question if the index I (T, T+D) is, for at least one of the analysis time windows Wn, above a predetermined threshold S (FIG. 3c). The definition of the threshold S can be arbitrary or adapted to the patient (preferably configurable by the physician) or even can be the result of an adaptive calculation being updated regularly. As a particular example of an adaptive threshold, one can consider a spontaneous atrial event (non-stimulated depolarization of the atrium) and calculate the indices I(0,30), I(15,45), I(30,60) . . . over a given period. The threshold S is then defined as being equal to 50% of the maximum value of all index values thus calculated. The threshold S may be recalculated at regular intervals, typically once a day, or on each atrial event validated by the device.

If the test is performed and used to prove the presence of an atrial contraction, the device determines the moment of the beginning and the end of the endocardiac acceleration peak EA4 component (PEA4). This can be obtained, for example, by considering the peak to extend from the first index value exceeding the threshold S until the last index value that is still located above the same threshold S as shown in FIG. 3c. In other words, when the index value for two successive windows is determined to be crossing downward of threshold S, the end time is thus determined based on such crossing.

The final moment of the EA4 peak endocardial acceleration component can be more finely searched with a series of sliding windows having a time lag of 5 milliseconds compared to the previous window. Once it was determined that one of these narrower sliding windows provided an index I below the threshold S, the end time of PEA4 peak can be selected as either the end of this window W or the moment of the beginning of that same window W (which makes it possible to integrate the protosystolic ventricular delay, a complex period during which mechanical ventricular ejection does not occur).

Once the start and the end of the of a PEA4 peak are determined, the end time may be used for setting the AVD so that the device stimulates the ventricle only after an atrial contraction has been actually completed.

FIG. 4 presents three examples of timing of an EA signal obtained, respectively, in the case of a too long AVD, an AVD properly adjusted, and a too short an AVD. It is noted that the term DAV on FIG. 4 is synonymous with the term AVD. FIG. 4a, illustrates the incidence of a too long AVD, which leaves a dead time X between the end of atrial contraction (demonstrated by the PEA4) and the beginning of ventricular contraction (resulting from stimulation V, which produces on the EA signal the PEA1 peak). FIG. 4b illustrates the case where the AVD has been adjusted to an optimal value, for counteracting the dead time X to trigger the contraction of the ventricle (applying V stimulation) immediately after its filling, that is to say at the end of the atrial contraction—corresponding to the EA signal at the end of the PEA4 peak. FIG. 4c illustrates a situation where the applied AVD presents too short value. In this case, the ventricle begins to contract before it has been completely filled, thereby decreasing the ejected volume, and thus the flow of the cardiac pump. On the EA signal, this situation is revealed by a merger of the PEA4 peak and of the PEA1 peak that immediately follows.

Knowing the moment when the PEA4 peak ends, it is then straightforward to give the AVD a value such that the ventricle is not stimulated before the end of the PEA4 peak, that is to say before the end of atrial contraction preceding this stimulation.

In a preferred embodiment, the AVD is adjusted to have such a value that it coincides with the moment of end of the PEA4 peak. Its value can be determined at each atrial cycle (detected or stimulated), or at regular intervals, typically once a day, possibly differentiating stimulated atrial events and spontaneous atrial events.

Alternatively, the device can determine not only the AVD as a function of the moment the PEA4 ends, but also as a function of the start time of the PEA1 that immediately follows. The calculated value of the AVD depends upon the time interval between these two moments PEA4 and PEA1, which can be determined so that the end time of the PEA4 matches with the start time of the PEA1 that immediately follows.

In another embodiment, the AVD is adjusted so that the end time of the PEA4 precedes the start time of the PEA1 that immediately follows by a predetermined period, typically 10 ms.

One skilled in the art will appreciate that the present invention can be practiced by embodiments other than those disclosed, which are presented for purposes of illustration and not of limitation.

The invention claimed is:

1. An active implantable medical device of the cardiac stimulation, resynchronization, cardioversion and/or defibrillation type, comprising:
   means for detecting spontaneous and stimulated atrial events;
   means for detecting ventricular events;
   means for calculating an atrio-ventricular delay AVD, said AVD starting on the detection of one of a spontaneous and a stimulated atrial event;
   an acceleration sensor having an output signal that is an EA signal representative of the movements produced by the contractions of the atrial cavity;
   means for analyzing the EA signal to identify and isolate in the EA signal an EA4 component corresponding to the fourth peak of endocardiac acceleration associated to the atrial activity, and means for calculating the value of the AVD based upon the EA4 component; and
   means for pacing the ventrical with a low energy stimulation pulse, in response to an expiration of the calculated AVD and in the absence of a detected spontaneous ventricular event,
   wherein the means for calculating the value of the AVD further comprises means for determining a parameter of the EA4 component as a function of an end time of the EA4 component, and calculating the value of the AVD as a function of said determined parameter.

2. The device of claim 1, wherein the value of the AVD is calculated so that the end of the AVD is at least concurrent with or subsequent to the end time of the EA4 component.

3. The device of claim 2, wherein the end of the AVD is defined by the end time of the EA4 component.

4. The device of claim 1 wherein the end of the AVD is calculated so that the end of the AVD is subsequent to the end time of the EA4 component.

5. The device of claim 1, wherein:
   the means for analyzing the EA signal further comprises means for recognizing and isolating in the EA signal an EA1 component corresponding to a first endocardial acceleration peak associated with the ventricular activity and for determining a start time of said EA1 component, and the value of the AVD is calculated based on the determined start time of the EA1 component.

6. The device of claim 5, wherein the value of the AVD is calculated based on the time interval between the end time of the EA4 component and the start time of the EA1 component immediately following.

7. The device of claim 6, wherein the value of the AVD is calculated so that the end time of the EA4 component matches the start time of the immediately following EA1 component.

8. The device of claim 6, wherein the value of the AVD is calculated so that the end time of the EA4 component precedes the start time of the immediately following EA1 component by a predetermined duration.

9. The device of claim 1, wherein the means for analyzing the EA signal further comprises means for quantifying a parameter (I) of the EA signal within at least one analysis time window (W) having a predetermined length, said window being triggered after the detection of the atrial event (P), and ending on another specific event.

10. The device of claim 9 wherein said another specific event is an event selected from among the group consisting of a ventricular detection, a ventricular stimulation, a detection of an EA1 signal, and a fixed period.

11. The device of claim 9 wherein the quantified parameter (I) is the energy of the EA signal integrated over the duration of the window (W).

12. The device of claim 9, wherein the means for analyzing the EA signal further comprises means for quantifying the parameter (I1 ... In) inside each of a plurality of temporally successive windows (W1 ... Wn).

13. The device of claim 12, wherein the temporally successive windows (W1 ... Wn) are windows overlapping in time.

14. The device of claim 12, wherein the means for analyzing the EA signal further comprises means for comparing the quantified parameters (I1 ... In) to a given threshold (S) and defining the end time of the EA4 component in response to the quantified parameters of successive windows crossing downward of said threshold.

15. The device of claim 14, wherein the threshold (S) is selected from among the group consisting of a fixed threshold; a parameterizable threshold; an adaptive threshold recalculated at regular intervals; and an adaptive threshold recalculated on each cycle comprising a valid atrial event.

16. The device of claim 1, wherein the acceleration sensor is selected from among the group consisting of an endocardial sensor; an epicardial sensor; and an external sensor.

* * * * *